(12) United States Patent
Roediger

(10) Patent No.: US 6,521,133 B1
(45) Date of Patent: Feb. 18, 2003

(54) PROCESS FOR THERMAL SLUDGE DISINFECTION

(75) Inventor: Markus Roediger, Sewickley, PA (US)

(73) Assignee: Roediger Pittsburgh, Inc., Allison Park, PA (US)

( * ) Notice: Subject to any disclaimer, the term of this patent is extended or adjusted under 35 U.S.C. 154(b) by 0 days.

(21) Appl. No.: 09/632,824

(22) Filed: Aug. 7, 2000

(51) Int. Cl.$^7$ ............................................... C02F 11/18
(52) U.S. Cl. ....................... 210/742; 210/744; 210/764; 210/774; 210/175; 210/916; 422/1; 422/38
(58) Field of Search ................................ 210/742, 770, 210/774, 764, 766, 175, 176, 180, 181, 744, 916; 422/1, 38

(56) References Cited

U.S. PATENT DOCUMENTS

| | | | |
|---|---|---|---|
| 4,925,571 A | * | 5/1990 | Jacob et al. ................. 210/742 |
| 5,618,442 A | * | 4/1997 | Christy ....................... 210/742 |
| 5,888,453 A | * | 3/1999 | Luker ......................... 210/179 |
| 6,103,191 A | * | 3/2000 | Luker ......................... 210/179 |
| 6,117,203 A | * | 9/2000 | Buchhave et al. .......... 210/742 |

* cited by examiner

*Primary Examiner*—Robert Popovics
(74) *Attorney, Agent, or Firm*—Ansel M. Schwartz

(57) ABSTRACT

The present invention pertains to a system for thermal disinfection of sludge with the aim of pathogen reduction. Such thermal sludge treatment systems require a certain minimum detention time t dependent on the temperature T of the heated sludge. The system according to the present invention is a continuous flow system. The system includes means for continuous sludge heating. The heated sludge flows continuously through at least one chamber, whereby the flow through the chamber has a substantially vertical direction. The mean residence time t2 of the sludge between entering the chamber and leaving the chamber is minimum 2 times the time period t required by regulations for conventional batch systems. The ratio of the flow path length of the flow through the chamber or chambers to the hydraulic diameter of the vertical flow through the chamber or chambers l/d is at least 3:1. The higher the ratio t2/t, the smaller can be the required ratio l/d. The relationship is: $l/d * t2/t > 8$.

20 Claims, 2 Drawing Sheets

PROCESS FOR THERMAL SLUDGE DISINFECTION

FIELD OF THE INVENTION

The present invention is related to thermal disinfection or pasteurization of liquid sludge, such as sewage sludge. Disinfection is the inactivation of pathogens to levels low enough so that the sludge can be beneficially used, e.g. for land application, without infection risks. Pasteurization is the disinfection of liquids by heat. Thermal disinfection requires maintenance of every sludge particle at a certain temperature T (above 50° C.) for a minimum time period t. The time period t depends on the temperature T, but should not be less than 30 minutes for sewage sludge, even if T is 70° C. or above. The Environmental Protection Agency (EPA) of the United States of America has published time-temperature relationships for thermal sludge treatment in Biosolids Rule 503. The present invention proposes a continuous flow system for thermal sludge disinfection complying with the EPA regulations and providing so-called Class A Biosolids.

The invention is related to various process combinations for thermal disinfection and stabilization of liquid sludge, e.g. thermal pre-pasteurization followed by anaerobic digestion, aerobic-thermophilic pre-pasteurization followed by anaerobic digestion, or temperature-phased thermophilic/mesophilic anaerobic digestion. In the latter process combination, the system according to the present invention is provided between the thermophilic and mesophilic digestion stages, whereby sludge heating occurs prior to or as part of the thermophilic digestion stage.

BACKGROUND OF THE INVENTION

Prior art knows batch systems for sludge pasteurization. Sludge is heated to a temperature T. After the temperature T is reached, batches of heated sludge are maintained in batch tanks at temperature T for a time period t. After the time period t has expired, sludge batches are removed from the tanks and cooled. If heat is provided continuously, a continuous sludge flow should be heated, e.g. in a heat exchanger. If a sludge flow is continuously heated, at least three batch tanks are required to provide the minimum residence time. While one tank is filled with heated sludge, the second tank is at rest providing the minimum batch detention time t, and the third tank is emptied. After every cycle with a duration of t, the tanks are exchanged: The filled first tank is now at rest, the second tank is now emptied, and the emptied third tank is now filled; and so on.

Such batch systems have several disadvantages. They require a complicated control system including at least 6 automatic valves and three level sensors. Synchronization of fill and draw pumps is difficult. There is an inherent danger of recontamination because each tank is periodically filled with not yet disinfected and therewith pathogen containing sludge. If only a little portion of the sludge in a tank, e.g. in a pipe connection or in the top of the tank, is not subject to the required temperature T for the required time t, the disinfection result might not be sufficient. While a tank is filled, air is displaced. The displaced air may not enter any of the other tanks because of the risk of recontamination. Therefore the air has to be vented to the atmosphere. This exhaust air is very odorous and requires deodorization. The airflow is the same as the sludge flow. Each tank must provide for the minimum detention time. The total volume of the three tanks is therefore $V=3*t*q$, whereby q is the sludge flow.

SUMMARY OF THE INVENTION

The present invention provides a pasteurization system with continuous flow. Sludge not only flows continuously through the heating means, but also through at least one chamber. These chamber or chambers provide for the required minimum residence time t at temperature T. No sludge particle is to leave the chambers before the minimum detention time t has expired. A single level sensor is sufficient to synchronize fill and draw pumps. Less automatic valves are required. Very little odorous air is displaced because the sludge level in the chamber is maintained almost constant and is changing only slowly dependent on the difference of the incoming and outgoing sludge flows.

A system according to the present invention comprises at least one chamber, however there can be more than one chambers, e.g. two or three chambers. The sludge from the sludge heater continually enters the first chamber. It can enter the chamber near its top or bottom. If it enters the first chamber at the top, it leaves the first chamber at the bottom, or vice versa. In this way, the sludge flows in a vertical, downward or upward direction through the first chamber. The same applies to all other chambers, whereby the flow through the last chamber has preferably a downward direction. The level in the last chamber is monitored and used to control the sludge withdrawal pump, i.e. synchronizing the sludge withdrawal flow with the sludge feed flow.

The new continuous flow system is easy to control and prevents recontamination by clearly separating a location where contaminated sludge enters the first chamber and another distant point where disinfected sludge leaves the last chamber. contaminated sludge is never in contact with disinfected sludge.

The flow through the chambers is slow; it is a so-called laminar flow. A laminar flow through a tube has a parabolic flow pattern. The velocity at the center of the tube is two times the average velocity, and the velocity at the wall is zero. The minimum residence time of all sludge particles is therefore half the mean residence time. The same applies to the flow through a non-circular chamber, whereby a hydraulic diameter is used instead of a real diameter. The hydraulic diameter is 4 times the cross sectional area divided by the perimeter. The mean detention time t2 in the chambers should be at least two times t. The fastest sludge particles have a detention time of minimum t. The total tank volume is $V=2*q*t$ and is therewith only ⅔ of the total tank volume of a batch system.

The slimmer the chambers, the lower the risk of short-circuiting. A single chamber should have a height to width ratio of minimum 3. Where several chambers are used, the flow path length l through these chambers should be at least 3 times the hydraulic diameter d.

While a slim chamber with a l/d ratio of 8 is sufficient for a t2/t ratio of 2, t2/t must be higher if the chamber is stout. In addition the product of $t2/t*l/d$ should be minimum of 8 and preferably 16. The average detention time t2 in a stout chamber with l/d=3 should be minimum 2.67*t for 8 or 5.33*t for 16. If e.g. T=70° C. and the required minimum detention time according to regulations is t=0.5 hours, the average detention time in a chamber with l/d=3 should be minimum of 1.3 hours and preferably 2.7 hours.

The flow pattern within the chambers can also be influenced by thermal convection. If the incoming sludge has a slightly higher temperature than the sludge in the chamber, the incoming sludge stratifies at the top and moves down in a layer as it cools down. Because the flow has approximately a plug-flow characteristic in this case, the minimum detention time is only slightly shorter than the mean detention time. It is therefore an advantage to have a downward flow.

On the other hand, sludge particles that are heavier than the bulk of the sludge sink relative to the sludge bulk. Therefore it is also beneficial to provide an upward flow in one of the chambers. In an upward flow, the detention time of heavy particles is longer than the average detention time. The analog consideration applies for sludge particles that are lighter than the bulk of the sludge. They are slower if the flow through the chamber is directed downwards.

Consequently, it is beneficial if at least one of the chambers has an upward flow, and another chamber has a downward flow.

Heavy particles, such as grit, can accumulate at the bottom of a chamber if the upward velocity is slower than the sedimentation velocity of these particles. Therefore it is suggested to periodically remove grit from the bottom by withdrawing sludge from every chamber bottom. Connections to the sludge withdrawal pump and automatic valves are proposed for this reason. It is recommended to provide chambers with a steep bottom, e.g. a conical bottom, so that grit can slide down to the connection in the bottom. To prevent short circuits, sludge feeding should be interrupted for a time period t before grit is removed from the chambers.

Floating matter, such as grease, could accumulate at the sludge surface, particularly in chambers with downward flow. By raising the sludge level to the overflow pipe level, scum can be removed through overflow pipes. The overflow pipe also serves as an emergency overflow, in case the level control should malfunction.

To prevent recontamination of treated sludge through air connections, air should not flow from one chamber to another chamber. This can be prevented by continuously sucking air through the top of all chambers and blowing the air into the atmosphere. However, the exhaust air is very odorous. Therefore it is suggested to provide check valves and vacuum breakers at the top of every chamber. If the sludge level in a chamber drops, air enters through the vacuum breaker. If the sludge level rises, air is forced through the check valve to the atmosphere. It is further recommended to deodorize the exhaust air, e.g. in a biofilter. The overflow pipes should be provided with water traps to prevent air leaving a chamber through an overflow pipe.

The incoming sludge flow can be heated to temperature T in a single step. It is also possible to heat it in two steps. It is beneficial to pre-heat the incoming sludge in a heat exchanger by simultaneous cooling of the effluent sludge. This serves for heat recovery and saves energy. In addition, depending on further sludge treatment, it can be necessary to cool the effluent sludge. The pre-heated sludge is then further heated to temperature T by another heating means, e.g. a hot water heat exchanger or by steam injection.

It is beneficial to have a high flow through the heating means. It is possible to re-circulate sludge through the heating means, whereby the incoming sludge is preferably blended with the re-circulated sludge before entering the heating means. It is also possible to use a high re-circulation flow to flush all heating means.

BRIEF DESCRIPTION OF THE DRAWINGS

In the accompanying drawings, the preferred embodiment of the invention and preferred methods of practicing the invention are illustrated in which.

DETAILED DESCRIPTION

Figure 1:
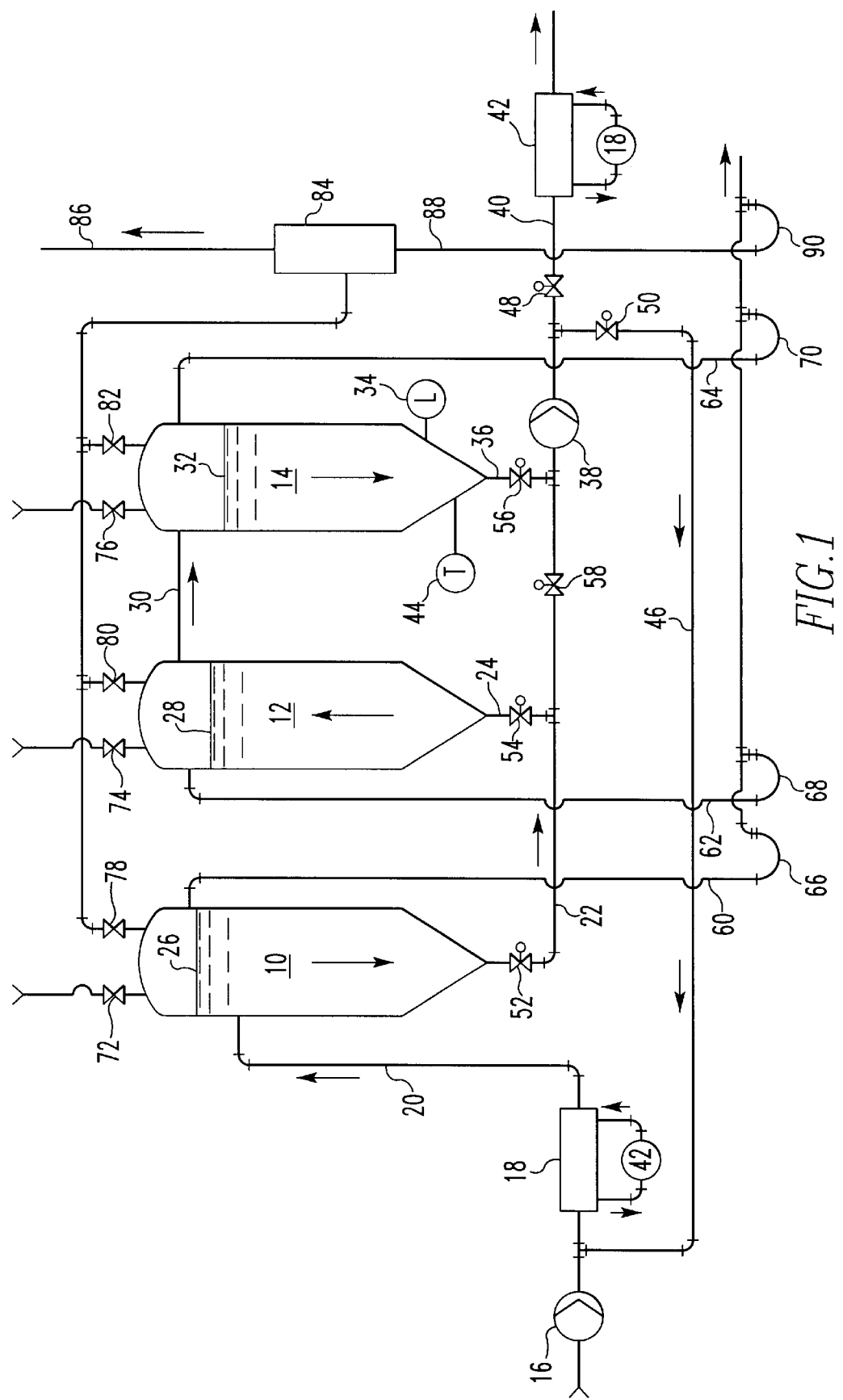
FIG. 1 shows a preferred embodiment of the invention is illustrated. The drawing shows a schematic flow diagram of the system according to the invention. This embodiment has a heating means, three chambers and a cooling means.

Referring now to the drawings wherein like reference numerals refer to similar or identical parts throughout the several views, and more specifically to FIG. 1 thereof, there is shown a thermal sludge disinfection system with continuous flow. A sludge flow of e.g. 5 $m^3/h$ is continuously pumped through three chambers 10,12 and 14. A pump 16 presses sludge through a heating means 18. Its temperature is raised from e.g. 10 to 65° C. This heating means could be a counter-flow sludge/water heat exchanger or another type of sludge heater. It could also or in addition include a sludge/sludge heat exchanger for heat recovery, heating incoming sludge by cooling outgoing treated sludge. The heated sludge is pumped through pipe 20 from heating means 18 to the first chamber 10. It enters chamber 10 near its top. The sludge flows downward through the first chamber 10. It flows by gravity from the bottom of the first chamber 10 through pipes 22 and 24 into the bottom of the second chamber 12. The sludge flows upwards through the second chamber 12. The sludge level 26 in the first chamber 10 is somewhat higher than the sludge level 28 in the second chamber 12. The sludge flows by gravity from the top of the second chamber 12 through pipe 30 to the top of the third and last chamber 14. It flows downward through the last chamber 14. The level 32 in the last chamber rises if the inflow exceeds the outflow, and drops if the outflow exceeds the inflow. A level sensor 34 in the last chamber 14 is therefore provided to synchronize outflow and inflow. The outflow is increased if the sludge level in chamber 14 rises, or vice versa. The sludge is withdrawn from the last chamber 14 through pipe 36 by pump 38 and forced through pipe 40 and cooler 42. Its temperature is reduced from 65° C. to e.g. 40° C. The cooled sludge may be pumped to further sludge treatment, e.g. into a conventional anaerobic mesophilic digester for sludge stabilization or vector attraction reduction. Preferably the heat removed in the cooler is used for preheating the incoming sludge.

The required minimum detention time of the sludge at a temperature T=65° C. is approx. 1 hour. Its average detention time t2 is minimum 2 hours. The three chambers have a net volume of 3.5 $m^3$ each, giving a total volume of 10.5 $m^3$. t2 is therefore 10.5 $m^3$/5 $m^3/h$=2.1 hours. Each chamber has a diameter d=1 m and a net cylindrical height h of 4.5 m. The length of the flow path through all chambers is l=3*h=13.5 m, and l/d*t2/t=13.5*2.1=28.35>8 and preferably 16. It would be possible to use stouter chambers. If they have a diameter d=1.15 m and a net cylindrical height h of 3.4 m, l=10.1 m, l/d=8.8, and l/d*t2/t=8.8*2.05=18. This is more than sufficient. The total vessel height would be approx. 5 m, including 1 m freeboard and conical bottom.

A temperature sensor 44 is provided near the exit of the last chamber 14 or in line 36. If the temperature of the sludge leaving the last chamber 14 is below the required minimum temperature T, the sludge is returned through pipe 46 to heater 18. Pump 16 is shut down, valve 48 is closed and valve 50 is opened in this case. Sludge is returned until temperature sensor 44 monitors sufficient temperature. Then normal operation is resumed, i.e. valve 48 is opened, valve 50 is closed and pump 16 started again.

Sludge is also returned through line 46 and heater 18 during start-up of the system. Normal operation begins after temperature sensor 44 has been monitoring sufficient temperature for a time period t.

Grit can be removed from chamber 10 through pipe 22 and pump 38. Valve 52 remains open, but valve 54 is closed; valve 36 is closed and valve 58 is opened. Grit can be removed from chamber 12 by closing valve 52 and opening valve 54. The duration of grit removal is short. Grit removal should take place after the system has been shut down for a minimum period of t to prevent short circuits.

The chambers have overflow pipes 60, 62 and 64 with syphons 66, 68 and 70. These syphons are filled with water and prevent odorous air flowing from the chambers through the overflow pipes. The overflow pipes serve not only for emergency overflow, but also provide a possibility for scum removal. They are connected to a sump (not shown).

On the top of the chambers, vacuum breakers 72, 74 and 76 are installed. They admit air into the chambers when the sludge levels drop. Air is displaced from the chambers through check valves 78, 80 and 82 when the sludge levels increase. The air is displaced through a deodorizer 84 and line 86 into the atmosphere. Condense water is removed from deodorizer 86 and drained through line 88 and syphon 90.

Figure 2:
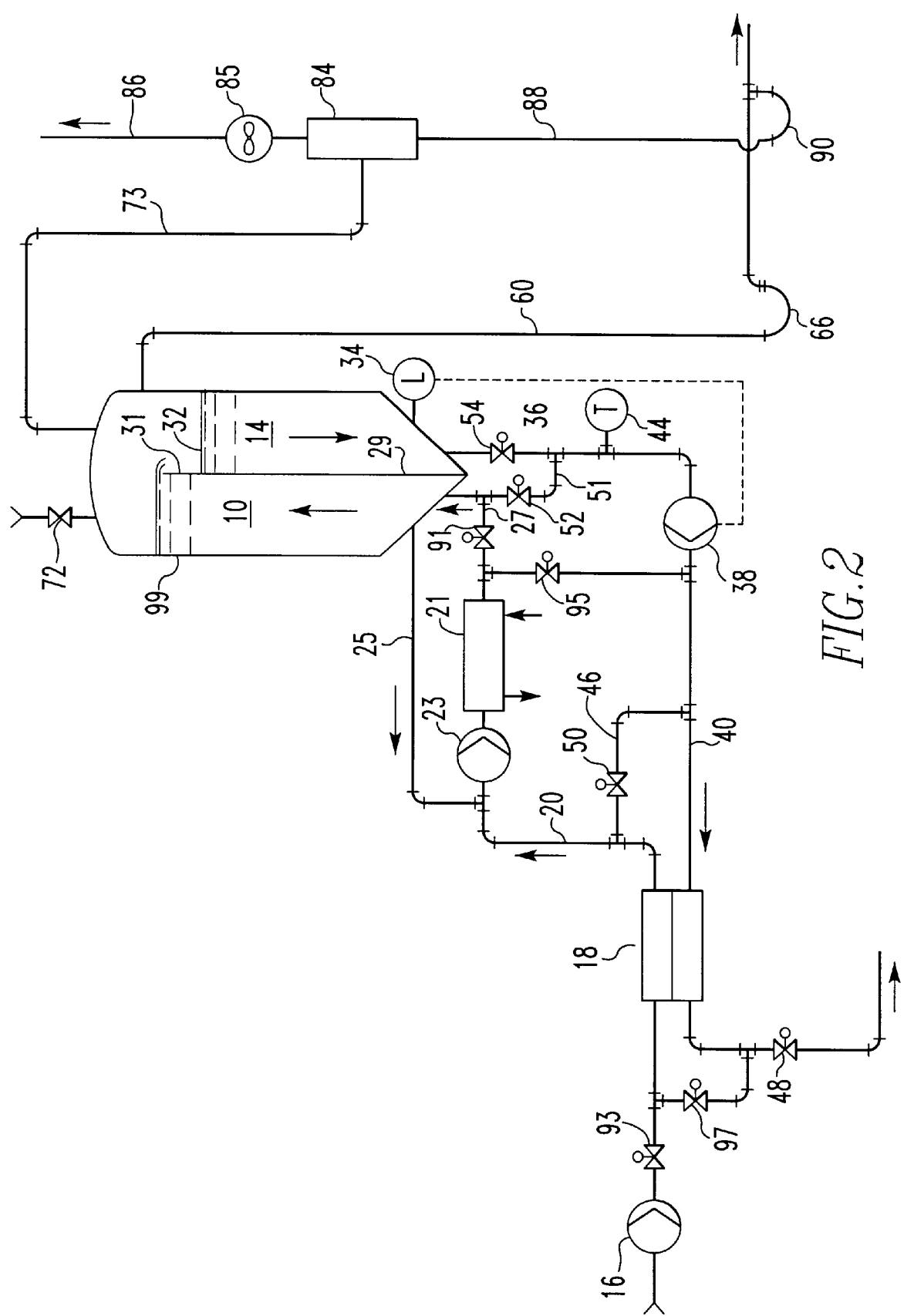
FIG. 2 shows another preferred embodiment of the invention. It includes a sludge/sludge heat exchanger for heat recovery, a heating means for further heating a blend of incoming and re-circulated sludge, and two chambers in a single tank.

Referring now to FIG. 2, there is shown another thermal sludge disinfection system with continuous flow. The sludge flows continuously through two chambers 10 and 14. A pump 16, usually a positive displacement pump, presses sludge through a pre-heating means 18. The peak flow through pump 16 may be 2 m$^3$/h. The preheating means 18 may be a counter-flow sludge/sludge heat exchanger for heat recovery. While cold influent sludge is pre-heated from e.g. 10° C. to 40° C., hot effluent sludge is cooled from e.g. 70° C. to 40° C. The pre-heated sludge is pumped through pipe 20 from heating means 18 to a second heating means 21. Heating means 21 uses external heat, e.g. hot water heat. A sludge recirculation pump 23, usually a centrifugal pump, recirculates sludge from the bottom of chamber 10 through pipe 25, heating means 21 and through pipe 27 back into the bottom of chamber 10. The capacity of the recirculation pump 23 can be much higher than the capacity of the sludge feeding pump 16, it can be e.g. 20 m$^3$/h. The mixed sludge entering the second heating means 21 would have a temperature of 67° C. and would be heated to 70° C.

The sludge having a temperature of e.g. 70° C. flows upwards through the first chamber 10. It overflows near the top of chamber 10 into the top of chamber 14. The chambers 10 and 14 are separated by a wall 29 that forms an overflow weir 31. The hot sludge flows downward through the chamber 14. The level 32 in the chamber 14 rises if the inflow exceeds the outflow, and drops if the outflow exceeds the inflow. A level sensor 34 in the chamber 14 is therefore provided to synchronize outflow and inflow, by changing the flow through a pump 38. The outflow through pump 38, usually another positive displacement pump, is increased if the sludge level in chamber 14 rises, or vice versa. The hot sludge leaves the last chamber 14 through pipe 36 and is withdrawn by pump 38 through pipe 40 and heat exchanger 18. The hot sludge is cooled in heat exchanger 18 by transferring heat into the inflowing cold sludge. The cooled sludge may have a temperature of e.g. 40° C. and is pumped to further sludge treatment, e.g. conventional anaerobic digestion for sludge stabilization or vector attraction reduction.

A temperature sensor 44 is provided near the exit of the chamber 14 or in line 36 or line 40. If the temperature of the sludge leaving the last chamber 14 is below a required minimum temperature of e.g. 70° C., the sludge is returned through pipe 46 to heater 21. Pump 16 is shut down, valve 48 is closed and valve 50 is opened in this case. Sludge is returned until temperature sensor 44 monitors sufficient temperature. Then normal operation is resumed, i.e. valve 48 is opened, valve 50 is closed and pump 16 started again.

Sludge is also returned through line 46 and heater 21 during start-up of the system. Normal operation begins after temperature sensor 44 is monitoring sufficient temperature for a time period t.

Grit can be removed from chamber 10 through pipe 51 and pump 38. Valve 52 is opened and valve 54 is closed. The duration of grit removal is short. Grit removal should take place after the system has been shut down for a minimum period of t to prevent short circuits.

The chambers 10 and 14 have a common overflow pipe 60 with a syphon 66. The syphon is filled with water to prevent odorous air flowing from the chambers through the overflow pipe. The overflow pipe 60 serves not only for emergency overflow, but also provides a possibility for scum removal. Pipe 60 is connected to a sump (not shown).

On the top of the chambers, a vacuum breaker 72 is installed. It admits air into the chambers when the sludge level 32 drops. Air is displaced from the chambers through line 73 when the sludge level 32 increases. The air is conveyed through a deodorizer 84, a ventilator 85 and line 86 into the atmosphere. Condense water that is removed in deodorizer 86 is drained through line 88 and syphon 90. The capacity of the ventilator 85 is at least equal to the capacity of pump 16, e.g. 2 m$^3$/h.

Both sides of heat exchanger 18 can be flushed with a high flow of hot sludge by means of pump 23. Valves 91, 52, 54, 48, 50 and 93 are closed and valves 95 and 97 are opened. Hot sludge is recirculated with high velocity from pump 23 through line 40, through one side of heat exchanger 18, through valve 97, through the other side of heat exchanger 18 and through line 20 back to pump 23.

With a sludge temperature in chambers 10 and 14 of 70° C., the minimum sludge detention time in the chambers is 30 minutes, according to EPA requirements, to guarantee sufficient pathogen reduction to achieve Class A biosolids. Considering a safety factor of 2, the volume of the chambers must be minimum 2 m3 to provide an average detention time of 1 hour in the chambers. Tank 99 including the chambers 10 and 14 could have a diameter of 0.8 m and a cylindrical height of 5 m. This height also includes a freeboard of around 1 m. The hydraulic diameter for vertical flow through chambers 10 and 14 is around 0.5 m. The ratio of the flow path length through both chambers to the hydraulic diameter of the chambers is about 16:1. This is a high ratio and sufficient to prevent short circuits.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for thermal sludge disinfection whereby pathogens present in the sludge are inactivated to levels low enough so that the sludge can be used without infection risks, said method comprising the steps of:

continuously pumping a sludge flow Q through at least one chamber, the chamber being connected to a heating means, the sludge having an average detention time t2 in a chamber volume V=Q*t2, and a flow path length l within the chamber and a hydraulic diameter d perpendicular along the flow path through the chamber;

continuously heating the continuous sludge flow Q with said heating means to a temperature T, wherein T is greater than $T_{min}$;

maintaining the sludge at said temperature T for a time period t, wherein t is greater than $t_{min}$, wherein $t_{min}$ and $T_{min}$ are preselected, and a known relationship between $t_{min}$ and $T_{min}$ exists, such that selection of $t_{min}$ or $T_{min}$ dictates the other in order to disinfect the sludge whereby pathogens present in the sludge are inactivated to levels low enough so that the sludge can be used without infection risks, wherein t2/t has a minimum value of 2, l/d has a minimum value of 3 and the product of t2/t and l/d has a minimum value of 8, thereby producing thermally disinfected sludge containing pathogens which have been inactivated to levels low enough so that the sludge can be used without infection risks; and continuously removing said thermally disinfected sludge.

2. A method for thermal sludge disinfecting according to claim 1 including a step of pre-heating the incoming sludge flow by cooling the thermally disinfected sludge in a heat exchanger means.

3. A method according to claim 2 wherein Tmin=50° C. and tmin=30 minutes.

4. A method for thermal sludge disinfection as described in claim 1 whereby the flow through at least one chamber has a substantially vertical direction.

5. A method for thermal sludge disinfection according to claim 1 whereby at least one chamber has a bottom and a top and an inflow connection and an outflow connection, one connection being located near the top of the chamber and the other connection being located near the bottom of the chamber.

6. A method for thermal sludge disinfection according to claim 1 including the step of flowing the sludge by gravity through the chamber, the top of the chamber being open to atmospheric pressure.

7. A method for thermal sludge disinfection according to claim 1 including the step of installing a level sensor to monitor a sludge level in the chamber.

8. A thermal sludge disinfection system according to claim 7 including the step of forcing sludge from a sludge heating means to the chamber and removing sludge from the chamber with a withdrawal pump, The level sensor synchronizing the feed and withdrawal pumps.

9. A method for thermal sludge disinfection according to claim 1 including the step of connecting the top of the chamber to the atmosphere through a vacuum breaker letting in air when there is a sub-atmospheric pressure in the chamber.

10. A method for thermal sludge disinfection according to claim 1 including the step of connecting the top of the chamber to atmosphere through a check valve which lets out air when there is a pressure higher than atmospheric pressure in the chamber.

11. A method for thermal sludge disinfection according to claim 1 including the step of deodorizing air leaving the chamber before being emitted into the atmosphere.

12. A method for thermal sludge disinfection according to claim 1 whereby the chamber is made of stainless steel and is thermally insulated.

13. A method for thermal sludge disinfection according to claim 1 whereby the chamber has a bottom with a slope of minimum 45° and a pipe connection at the lowest point of the bottom.

14. A method for thermal sludge disinfection according to claim 1 whereby at least two chambers are compartments of a tank and separated by a wall.

15. A method for thermal sludge disinfection according to claim 1 including the step of re-circulating the sludge leaving the chamber through a heating means for sludge beating and back to the chamber when the temperature of the sludge leaving the chamber is below the temperature T.

16. A method for thermal sludge disinfection according to claim 1 including the step of transferring heat from the sludge leaving the chamber to the incoming cold sludge for pre-heating with a heat exchanger.

17. A thermal sludge disinfection system according to claim 1 including the step of recirculating sludge with a recirculation pump from the chamber through heating means and back into the chamber.

18. A method for thermal sludge disinfection according to claim 17 including the step of mixing incoming sludge flow with re-circulating sludge flow upstream of the heating means.

19. A method for thermal sludge disinfection according to claim 18 including the step of pre-heating the incoming sludge flow before being mixed with the re-circulating sludge flow.

20. A thermal sludge disinfection system according to claim 1 including the step of re-circulating sludge with a re-circulation pump through heating means for flushing the heating means.

* * * * *